United States Patent [19]

Baker

[11] Patent Number: 4,783,351

[45] Date of Patent: Nov. 8, 1988

[54] TREATED SUBSTRATES

[76] Inventor: Marion A. Baker, 18161 Windsor Ave., Orange, Calif. 92667

[21] Appl. No.: 93,796

[22] Filed: Sep. 4, 1987

[51] Int. Cl.$^4$ ............................................. A01N 3/00
[52] U.S. Cl. ........................................ 428/17; 427/4; 428/24
[58] Field of Search ....................... 427/4; 428/17, 24; 47/DIG. 2

[56] References Cited

U.S. PATENT DOCUMENTS

| 2,567,929 | 9/1951 | Fessend | 427/4 |
| 4,278,701 | 7/1981 | Von Hagens | 427/4 |

FOREIGN PATENT DOCUMENTS

| 39792 | 3/1957 | Poland | 427/4 |
| 533357 | 2/1941 | United Kingdom | 427/4 |

Primary Examiner—Sam Silverberg
Attorney, Agent, or Firm—Joseph E. Mueth

[57] ABSTRACT

The process of obtaining preserved flower blooms and other natural predominantly carbohydrate products such as flower stems, leaves and vegetables which are free standing and have a natural fresh and/or esthetically attractive appearance maintained over prolonged periods which comprises removing most or substantially all of the water present in the substrate, and exposing the substantially dried substrate to a thermoplastic elastomeric polymer capable of forming sparingly chemically linked or non-chemically bonded links with itself.

The process enhances dried materials including most ornamental blooms such as roses, orchids, tulips, daffodils, lillies and many others, as well as more traditional, usually air-dried plants such as gypsophila, statis, eucalyptus, larkspur, strawflowers, cornflowers, caspia, horsetail (equisetum arvense joint grass), etc.

35 Claims, No Drawings

TREATED SUBSTRATES

BACKGROUND OF THE INVENTION

In my copending U.S. patent application Ser. No. 61,916 filed June 11, 1987, the disclosure of which is incorporated herein by reference, there is described a novel method of preserving flowers and other similar active-hydrogen containing substrates by first dehydrating the substrate to remove all or substantially all of the water present, followed by exposing the dried substrate to a cross-linking compound, for example, a di- or polyisocyanate (functionality of more than one) which react with the active hydrogen compounds naturally present in the substrate to form a three dimensional cross-linked polymeric network between the active hydrogen groups of the substrate and the polyfunctional isocyanate. This procedure yields a flower or other predominantly carbohydrate substrate which is free standing and has a natural fresh, and/or esthetically attractive appearance which is maintained over a prolonged period of weeks or months, or longer.

I have now discovered another and entirely unique approach to the problem of preserving carbohydrate substrates. More particularly, I have found a new and different way of preserving such substrates to provide preserved flowers and the like which are better looking and more long lasting than any heretofore believed possible.

It is believed that the present invention represents a major advance in this art, and that it will rapidly achieve great commercial significance.

SUMMARY OF THE INVENTION

Briefly, the present invention comprises the process of obtaining preserved flower blooms and other natural predominantly carbohydrate products such as flower stems, leaves and vegetables which are free standing and have a natural fresh appearance maintained over prolonged periods which comprises removing most or substantially all of the water present in the substrate, and exposing the substantially dried substrate to a thermoplastic elastomeric polymer capable of forming sparingly chemically linked or non-chemically bonded links with itself.

This invention also includes the produce prepared by removing most or substantially all of the water present in a substantially carbohydrate substrate, and exposing the substantially dried substrate to an elastomeric polymer capable of forming sparingly chemically linked or non-chemically bonded links with itself.

It is an object of this invention to provide a new method of preserving flowers and other predominantly carbohydrate substrates.

It is a further object of this invention to provide more esthetically attractive preserved flowers and other carbohydrate substrates.

It is yet another object of this invention to provide a longer lasting, more flexible, less frangeable, preserved carbohydrate substrate.

These and other objects and advantages of this invention will be apparent from the more detailed description which follows.

DESCRIPTION OF THE PREFERRED EMBODIMENTS

Substrates such as flow blooms, flower stems, leaves and vegetables are first substantially dried or dehydrated as described in my copending patent application, identified hereinabove. This procedure which may involve contact with alcohol after the thicker sections have been pierced to provide access holes for the alcohol to reach the interior of the flower is fully applicable to this invention. Other weed-like substrates such as gypsophilea, statis, eucalyptus, larkspur, straw flowers, caspia, horsetail are not dehydrated with alcohols. Instead they are freeze dried, or exposed to low-humidity air, silica gel, borax or other drying agents, often in a closed or controlled atmosphere.

The elastomeric polymers used in the practice of my invention are either physically (non-chemically, including hydrogen bonding) cross-linked, or chemically cross-linked. Each of these two types is discussed separately below in more detail. As used herein, sparingly cross-linked means up to about 5% of the elastomeric portion by weight, and preferably from about 1% to 3%.

1. Non-Chemical Crosslinking

The elastomeric polymers are thermoplastic elastomers having dissimilar domains as explained as follows. They are physically cross linked within themselves and are thus closely related to the effect achieved by the process described in my pending patent application identified above. There are however, several important differences: (1) The elastomeric polymers of this invention do not chemically bond, i.e.—(cross link) with the cellulose in the bloom. (2) The elastomeric polymers exhibit permanent set characteristics of a thermoplastic—not thermosets, as my prior work does, and they are therefore easier to permanently deform with either physical pressure or high temperature. (3) Since the elastomeric polymers do not contain either acid or base they have virtually no effect upon the color of the treated bloom, which is often not the case with chemically cross linked systems. (4) Blooms treated with the elastomeric polymers are quite flexible and do not require a post treatment coating to flatten their appearance—they also have a warm and pleasant "hand".

The blooms are unaffected by humidity or short duration immersion in water—an important commercial point. The use of additives such as antioxidants and ultraviolet stabilizers further ensures a considerable life span for the product under normal use conditions.

There are several major classes of thermoplastic rubbers. The largest and first developed one is called linear SBS thermoplastic rubbers which have properties similar to the branched or "star" SBS thermoplastic rubbers that were introduced almost simultaneously. These materials are made by polymerizing "blocks" of polystyrene with "blocks" of polybutadiene—thus, the nickname "block co-polymers".

Block co-polymers are also made from polystyrene and polyisoprene, commonly referred to as SIS polymers.

The SBS and SIS polymers can be hydrogenated to form polystyrene/polyolefin copolymers. It is this latter class that I find most useful because they do not contain the residual ethylenic double bond that is present in SBS and SIS polymers.

The hydrogenated polymers such as one having an ethylene-butylene structure is better for my use than the original SBS polymer because it does not degrade as rapidly and also because it is not as elastomeric and soft as comparable SBS or SIS polymer, and as a result, resists deformation from physical pressure or high temperatures to a greater degree.

More particularly, the thermoplastic elastomeric polymers capable of forming non-chemical cross links or bonds with itself is exemplified by block copolymers having individual polymeric chains of three blocks, a flexible block in the center and a thermoplastic block at each end of the chain, or two blocks (a diblock polymer) having a flexible block and one crystalline thermoplastic end block. In addition, the flexible and crystalline thermoplastic blocks can be variously arranged in, for example, a linear alternating sequence, or the blocks can be arranged wherein there are multiple ends.

The typical end blocks are made up of polystyrene, that is, repeating units having the formula:

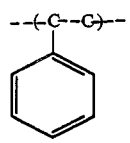

Preferably, the flexible block is in the center, and the "mid block" has a polybutadiene, polyisoprene, polyethylene, polybutylene, ethylene-propylene copolymer, or ethylene-butylene copolymer structure. The saturated structures are preferred in this situation.

The preferred polymers of the described class are available from Shell Chemical Company under the trademark "Kraton." Typical polybutadiene mid block polymers are known as Kraton D1101 & D1102. A typical polyisoprene type is known as Kraton D1107. Typical butylene types are known as Kraton G1650 and G1652. Typical ethylene-butylene types are known as Kraton G1726.

The physical cross linking occurs at the polystyrene end blocks. The polystyrene end blocks are present in minor proportion (about 10% to 35% by weight of total polymer) and are thermodynamically incompatible with the elastomeric mid block. The polystyrene end blocks having a glass transition temperature above room temperature, around 200 degrees F. The elastomeric mid block has a glass transition temperature well below room temperature. The polystyrene end blocks unite to form microscopic particles which has the effect of physically united many chains of the block copolymer. The particles or agglomerated polystyrene are called polystyrene domains and are uniformly distributed throughout the mass or film of polymer. The effect is to create a cross bonded network where the crosslinking is physical rather than chemical.

The rubber mid blocks are held in place, that is, immobilized by the polystyrene domains. Since the cross-linking is physical, it is reversible so that these rubber polymers can be heated, cooled, and solvated with loss, regain and/or change of properties.

These block copolymers are quite stable, provide a beautiful appearance or finish on flowers and other carbohydrate substrates, and afford a natural feel or "hand" to the preserved product.

The block copolymers are of relatively low molecular weight, form good solutions in solvent with viscosities such that with one or two dips, the substrate is sufficiently coated. The following are typical properties:

| Kraton G-1726 | |
| --- | --- |
| Tensile strength, psi[1] | 350 |
| Elongation, %[1] | 200 |
| Hardness, Shore A | 75 |
| Specific gravity | 0.91 |
| Brookfield viscosity, cps @ 77° F.[3] (Toluene solution) | 200 |
| Styrene/rubber weight ratio | 30/70 |
| Physical Form | Pellet |

[1]ASTM D 412 - tensile tester jaw separation speed 10 in./minute.
[2]Typical properties determined on case film from toluene solution.
[3]Kraton rubber at 25% w solids.

G-1650 and G1652 possess much higher tensile strength, elongation and viscosity due to their higher molecular weight. Conventional rubbers are much higher even than g-1650 and G1652 in viscosity. This increase in viscosity renders these polymers less economically useful for the herein described purposes.

The following examples are presented solely to illustrate the invention.

EXAMPLE I

Six fully opened "bridal pink" rose blooms and six fully opened "Privet" rose blooms with holes drilled in receptacles were placed in a plastic pail containing five gallons of anhydrous isopropyl alcohol, in which had been previously dissolved 4 ounces of clarified "Navel Jelly" marketed by Duro Corporation, and 2 ounces Ciba-Geigy Antioxidant "Irganox 245". The temperature of the alcohol was 35 degrees F. and it was maintained at the temperature for 48 hours. The flower blooms were removed from the alcohol, the excess alcohol adhering to the blooms was removed by a dry nitrogen gas jet and the blooms were placed in a commercial 40 gallon polyethylene garbage bag which also contained about 3 pounds of a desiccant clay. The bag was inflated with dry nitrogen gas, tied shut, and placed in front of an oscillating fan for 48 hours (temp. 65-80). The blooms were then removed and dipped in a 20 percent solution of Kraton G1726, the solvent being 40 percent toluene and 60 percent mixed heptanes. The solution also contained 0.2 percent Irganox 1010 antioxidant, 0.2 Tinuvin 328 Ultraviolet light absorber, and 0.2 percent Tinuvin light stabilizer. After dipping the blooms were drained and dried in ambient temperature moving air for a few hours to several days. They were then displayed.

The following are further and preferred embodiments:

Soaking in alcohol: combination of an antioxidant and phosphoric acid helps stabilize the color of the bloom.

Any of the elastomeric block copolymers can be extended with oil, resins and fillers in the manner that is employed with chemically cross-linked rubbers. However, oil extension results in poorer tensile strength and better lubricity and therefore oil extended rubbers are easier to distort, so I prefer to use the Kraton without oil extension for rose bloom preservation, but oil extension does produce a product that is more acceptable for leaf and stem preservation, or for some traditional dried plant materials such as Eucalyptus leaves and stems.

Normally, pigments are not required with Kraton, since it produces a flat finish without any modification. However, when it is extended with oils or other plasticisors or resins such as maleic anhydride/rosin adducts or styrene/allyl alcohol copolymers it is often desirable to add a flatting pigment. I have found that the normal flatting pigments are quite opaque and high the natural colors of the bloom. I have found that very pure fumed silica pigments and particulate polypropylene function well as flatting agents and are much more transparent than the more common flatting pigments (calcium carbonate is one example).

2. Chemical Crosslinking

The invention is also applicable to elastomers which are self cross-linked by use of rubber vulcanizing agents such as peroxides or upon exposure to gamma irradiation. The invention as already described is fully applicable to this embodiment. The preferred elastomers are polyisoprene, polybutadiene and butadiene-styrene random copolymer. The peroxide can be dicumyl peroxide as well as others known in the art.

EXAMPLE II

Four fully opened "bridal pink" rose blooms and four fully opened "Privet" rose blooms were placed in a plastic pail containing five gallons of anhydrous isopropyl alcohol, in which had been previously dissolved 4 ounces of clarified and 2 ounces Ciba-Geigy Antioxidant "Irganox 245". The temperature of the alcohol was 35 degrees F. and it was maintained at that temperature for 48 hours. The flower blooms were removed from the alcohol, the excess alcohol adhering to the blooms was removed by a dry nitrogen gas jet and the blooms were placed in a commercial 40 gallon polyethylene garbage bag which also contained about 3 pounds of a desiccant clay. The bag was inflated with dry nitrogen gas, tied shut, and placed in front of an oscillating fan in my laboratory for 48 hours (temp. 65–80). The blooms were then removed and dipped in a 5 percent solution of styrenebutadiene random copolymer polymer, the solvent being toluene. After dipping the blooms were drained and dried in ambient temperature moving air for a few hours. They were then exposed to gamma radiation for 10 hours.

EXAMPLE III

Ambient air dried gypsophilea is dipped in Kraton G-1726X—10% solution in 30% toluene—70% mixed hexanes and then rid of solvent by evaporation in ambient air.

Imparts toughness, better handling for easier arranging and little loss of blooms when crushed or roughly handled.

EXAMPLE IV

Ambient air dried "Silver Dollar Eucalyptus" is dipped in Kraton G-1726 (100 parts) and Tufflo 6206 (ARCO) or Shell Flex 371 (Shell) oil (20 parts), total solids 10% in 505 toluene—50% mixed hexanes and then air dried.

Imparts flexibility, toughness and better handling.

Having fully described the invention, it is intended that it be limited only by the lawful scope of the appended claims.

I claim:

1. The process of obtaining preserved flower blooms and other natural predominantly carbohydrate products such as flower stems, leaves and vegetables which are free standing and have a natural fresh and/or esthetically attractive appearance maintained over prolonged periods which comprises removing most or substantially all of the water present in the substrate, and exposing the substantially dried substrate to a thermoplastic elastomeric polystyrene/polymonoolefin or polydiolefin block copolymer capable of forming non-chemically bonded links with itself, or a thermoplastic elastomeric polydiolefin or styrene-diolefin random copolymer capable of forming sparingly chemically links with itself and wherein said thermoplastic elastomeric polydiolefin or styrenediolefin random copolymer is springly cross linked.

2. The product of the process of claim 1.

3. The process of claim 1 wherein the elastomeric polymer is a block copolymer having polystyrene end blocks and a flexible mid block which forms non-chemically bonded links with itself.

4. The process of claim 1 wherein the elastomeric polymer is a block copolymer having at least one flexible block and at least one polystyrene block.

5. The product of the process of claim 3.

6. The product of the process of claim 4.

7. The process of claims 3 or 4 wherein the flexible mid block is polybutadiene.

8. The process of claims 3 or 4 wherein the flexible mid block is polybutylene.

9. The process of claims 3 or 4 wherein the flexible mid block is polyisoprene.

10. The process of claims 3 or 4 wherein the flexible mid block is ethylene-1,butene copolymer.

11. The process of claims 3 or 4 wherein the flexible mid block is ethylene-propylene copolymer.

12. The product of the process of claim 7.

13. The product of the process of claim 8.

14. The product of the process of claim 9.

15. The product of the process of claim 10.

16. The product of the process of claim 11.

17. The process of claim 1 wherein the elastomeric polymer is a vulcanizable elastomer.

18. The product of the process of claim 17.

19. The process of claim 1 wherein the elastomeric polymer is chemically crosslinked by a rubber vulcanizing agent.

20. The process of claim 1 wherein the elastomeric polymer is chemically cross linked by exposure to gamma irradiation.

21. The process of claim 1 wherein the elastomeric polymer is selected from the group consisting of polyisoprene, polybutadiene, and styrene-butadiene random copolymer.

22. The product of the process of claim 19.

23. The product of the process of claim 20.

24. The product of the process of claim 21.

25. The product of claim 2 which are treated with fumed silica pigments or particulate polypropylene.

26. The product of claim 2 which is subsequently coated with surface coatings such as leather lacquers containing fumed silica pigments or particulate polypropylene.

27. The process of claim 1 wherein the substrate is first pierced to provide access holes and then substantially dehydrated to remove most or substantially all of the water.

28. The process of claim 1 wherein the substrate is roses, orchids, tulips, daffodils, lillies and other ornamental blooms as well as gypophila, statis, eucalyptus, larkspur, strawflowers, cornflowers, caspia, or horsetail.

29. The product of claim 28.

30. The process of claim 1 wherein the substrate is a flower bloom.

31. The product of claim 30.

32. The process of claim 1 wherein the substrate is vegetable stem and/or vegetable leaf.

33. The process of claim 1 wherein the substrate prior to water removal is a bloom, leaf and/or stem in its unaltered and natural state.

34. The process of claim 1 wherein the substrate additionally is treated with antioxidants, antiozonants, ultraviolet stabilizers, heat stabilizers, light absorbers and/or optical brighteners.

35. The process of claim 1 wherein said elastomeric polymer is oil extended.

* * * * *

UNITED STATES PATENT AND TRADEMARK OFFICE
CERTIFICATE OF CORRECTION

PATENT NO. : 4,783,351
DATED : November 8, 1988
INVENTOR(S) : Marion A. Baker

It is certified that error appears in the above-identified patent and that said Letters Patent is hereby corrected as shown below:

Page 1 Cancel "Ave." insert --Drive--

Column 1 Line 46 Cancel "produce" insert --product--

Column 3 Line 48 Cancel "united" insert --uniting--

Column 4 Line 29 Cancel "Navel" insert --Naval--

Column 5 Line 2 Cancel "high" insert --hide--

Signed and Sealed this

Twenty-third Day of May, 1989

Attest:

DONALD J. QUIGG

Attesting Officer     Commissioner of Patents and Trademarks